US012784204B2

(12) United States Patent
Wang

(10) Patent No.: US 12,784,204 B2
(45) Date of Patent: Nov. 3, 2026

(54) INFORMATION PROCESSING APPARATUS, OPERATION METHOD OF INFORMATION PROCESSING APPARATUS, OPERATION PROGRAM OF INFORMATION PROCESSING APPARATUS, PREDICTION MODEL, LEARNING APPARATUS, AND LEARNING METHOD

(71) Applicant: FUJIFILM CORPORATION, Tokyo (JP)

(72) Inventor: Caihua Wang, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 235 days.

(21) Appl. No.: 18/673,322

(22) Filed: May 24, 2024

(65) Prior Publication Data

US 2024/0312011 A1 Sep. 19, 2024

Related U.S. Application Data

(63) Continuation of application No. PCT/JP2022/040266, filed on Oct. 27, 2022.

(30) Foreign Application Priority Data

Dec. 21, 2021 (JP) ................................ 2021-206988
Jul. 26, 2022 (JP) ................................ 2022-119116

(51) Int. Cl.
*G06T 7/00* (2017.01)
*G06T 7/11* (2017.01)
(Continued)

(52) U.S. Cl.
CPC .............. *G06T 7/0012* (2013.01); *G06T 7/11* (2017.01); *G06V 10/44* (2022.01); *G16H 50/20* (2018.01);
(Continued)

(58) Field of Classification Search
CPC .................... G06T 7/0012; G06T 7/11; G06T 2207/10088; G06T 2207/30016; G16H 50/20; G06V 10/44
(Continued)

(56) References Cited

U.S. PATENT DOCUMENTS

2010/0014756 A1 1/2010 Kato et al.

FOREIGN PATENT DOCUMENTS

CN 113781390 A 12/2021
JP 2010-017274 A 1/2010

OTHER PUBLICATIONS

Liu, Mingxia, et al. "Joint classification and regression via deep multi-task multi-channel learning for Alzheimer's disease diagnosis." IEEE Transactions on Biomedical Engineering 66.5 (2018): 1195-1206. (Year: 2018).*

(Continued)

*Primary Examiner* — Jonathan S Lee
(74) *Attorney, Agent, or Firm* — SOLARIS Intellectual Property Group, PLLC

(57) ABSTRACT

An information processing apparatus includes a processor, in which the processor acquires a medical image showing an organ of a subject and disease-related data of the subject, subdivides the medical image into a plurality of patch images, uses a prediction model including a feature amount extraction unit that extracts a feature amount from the patch images and the disease-related data and a correlation information extraction unit that extracts at least correlation information between the plurality of patch images and correlation information between the plurality of patch images and the disease-related data, and inputs the patch images and the disease-related data to the prediction model and outputs a prediction result regarding a disease from the prediction model.

9 Claims, 11 Drawing Sheets

(51) Int. Cl.
*G06V 10/44* (2022.01)
*G16H 50/20* (2018.01)

(52) U.S. Cl.
CPC ............... *G06T 2207/10088* (2013.01); *G06T 2207/30016* (2013.01)

(58) Field of Classification Search
USPC .......................................................... 382/128
See application file for complete search history.

(56) References Cited

OTHER PUBLICATIONS

Li, Yafeng, et al. "A method for predicting alzheimer's disease based on the fusion of single nucleotide polymorphisms and magnetic resonance feature extraction." International Workshop on Multimodal Learning for Clinical Decision Support. Cham: Springer International Publishing, 2021. (Year: 2021).*

Goto, Tsubasa et al."Multi-modal deep learning for predicting progression of Alzheimer's disease using bi-linear shake fusion" Proc. of SPIE, vol. 11314, 2020.

Wang, Xiaosong et al. "Self-supervised Image-text Pre-training With Mixed Data In Chest X-rays" [online].Mar. 30, 2021, [retrieval date Dec. 19, 2022], Internet<URL:https://arixiv.org/pdf/2103.16022.pdf>.

Dosovitskiy, Alexey et al.," An Image is Worth 16×16 Words:Transformers for Image Recognition at Scale" conference paper at ICLR 2021, [online].Jun. 3, 2021, [retrieval date Dec. 19, 2022], Internet:<URL:https://arxiv.org/pdf/2010.11929.pdf>.

International Search Report issued in International Application No. PCT/JP2022/040266 on Jan. 10, 2023.

Written Opinion of the ISA issued in International Application No. PCT/JP2022/040266 on Jan. 10, 2023.

* cited by examiner

INFORMATION PROCESSING APPARATUS, OPERATION METHOD OF INFORMATION PROCESSING APPARATUS, OPERATION PROGRAM OF INFORMATION PROCESSING APPARATUS, PREDICTION MODEL, LEARNING APPARATUS, AND LEARNING METHOD

CROSS-REFERENCE TO RELATED APPLICATIONS

This application is a continuation application of International Application No. PCT/JP2022/040266, filed on Oct. 27, 2022, the disclosure of which is incorporated herein by reference in its entirety. Further, this application claims priority from Japanese Patent Applications No. 2021-206988, filed on Dec. 21, 2021, and No. 2022-119116, filed on Jul. 26, 2022, the disclosures of which are incorporated herein by reference in their entireties.

BACKGROUND

1. Technical Field

The technology of the present disclosure relates to an information processing apparatus, an operation method of an information processing apparatus, an operation program of an information processing apparatus, a prediction model, a learning apparatus, and a learning method.

2. Description of the Related Art

In response to the advent of a full-fledged aging society, development of a prediction model that supports a diagnosis of a disease, such as dementia typified by Alzheimer's dementia, or predicts progression of dementia is being vigorously promoted. For example, in <Goto, T., Wang, C., Li, Y. & Tsuboshita, Y. Multi-modal deep learning for predicting progression of Alzheimer's disease using bi-linear shake fusion, Proc. SPIE (Medical Imaging) 11314, 452 to 457 (2020).>, a so-called multimodal prediction model that receives a tomographic image (hereinafter, referred to as an MRI image) obtained by capturing a brain of a subject for which progression of dementia is to be predicted using magnetic resonance imaging (MRI) and dementia-related data such as an age, sex, genetic test data, and cognitive function test data (cognitive ability test score) of the subject and that outputs a prediction result of the progression of the dementia is disclosed.

SUMMARY

The brain has various anatomical regions such as a hippocampus, a parahippocampal gyrus, an amygdala, a frontal lobe, a temporal lobe, and an occipital lobe. A relationship between each anatomical region and a cognitive ability is different. However, the prediction model disclosed in <Goto, T., Wang, C., Li, Y & Tsuboshita, Y Multi-modal deep learning for predicting progression of Alzheimer's disease using bi-linear shake fusion, Proc. SPIE (Medical Imaging) 11314, 452 to 457 (2020).> handles an MRI image showing the entire brain and does not take the anatomical region into consideration.

For this reason, a method of subdividing the MRI image into a plurality of patch images and input to the prediction model, and extracting a feature amount of each of the plurality of patch image from the prediction model is considered. However, even in a case where this method is adopted, in the prediction model disclosed in <Goto, T., Wang, C., Li, Y & Tsuboshita, Y Multi-modal deep learning for predicting progression of Alzheimer's disease using bi-linear shake fusion, Proc. SPIE (Medical Imaging) 11314, 452 to 457 (2020).>, it is not possible to use correlation information between the plurality of patch images and correlation information between the plurality of patch images and the dementia-related data (in a case where there are a plurality of pieces of the dementia-related data as described above, correlation information between the plurality of pieces of dementia-related data is included) for the prediction due to structural reasons, and a prediction accuracy of the progression of the dementia could not be increased significantly.

One embodiment according to the technology of the present disclosure provides an information processing apparatus, an operation method of an information processing apparatus, an operation program of an information processing apparatus, a prediction model, a learning apparatus, and a learning method capable of improving a prediction accuracy of a prediction result related to a disease by a prediction model.

According to the present disclosure, there is provided an information processing apparatus comprising: a processor, in which the processor acquires a medical image showing an organ of a subject and disease-related data of the subject, subdivides the medical image into a plurality of patch images, uses a prediction model including a feature amount extraction unit that extracts a feature amount from the patch images and the disease-related data and a correlation information extraction unit that extracts at least correlation information between the plurality of patch images and correlation information between the plurality of patch images and the disease-related data, and inputs the patch images and the disease-related data to the prediction model and outputs a prediction result regarding a disease from the prediction model.

It is preferable that the prediction model includes a transformer encoder that takes in input data in which the patch images and the disease-related data are mixed and extracts the feature amount.

It is preferable that the feature amount extraction unit includes a self-attention mechanism layer of the transformer encoder, and the correlation information extraction unit includes a linear transformation layer that linearly transforms the input data to the self-attention mechanism layer to obtain first transformation data, an activation function application layer that applies an activation function to the first transformation data to obtain second transformation data, and a calculation unit that calculates a product of output data from the self-attention mechanism layer and the second transformation data for each element as the correlation information.

It is preferable that the disease is dementia, the medical image is an image showing a brain of the subject, and the processor extracts a first region image including a hippocampus, an amygdala, and an entorhinal cortex and a second region image including a temporal lobe and a frontal lobe from the medical image, and subdivides the first region image and the second region image into the plurality of patch images.

It is preferable that the disease is dementia, the medical image is morphological image test data, and the disease-related data includes at least one of an age, a sex, blood/cerebrospinal fluid test data, genetic test data, or cognitive function test data of the subject.

It is preferable that the morphological image test data is a tomographic image obtained by a nuclear magnetic resonance imaging method.

According to the present disclosure, there is provided an operation method of an information processing apparatus, the operation method comprising: acquiring a medical image showing an organ of a subject and disease-related data of the subject; subdividing the medical image into a plurality of patch images; using a prediction model including a feature amount extraction unit that extracts a feature amount from the patch images and the disease-related data and a correlation information extraction unit that extracts at least correlation information between the plurality of patch images and correlation information between the plurality of patch images and the disease-related data; and inputting the patch images and the disease-related data to the prediction model and outputting a prediction result regarding a disease from the prediction model.

According to the present disclosure, there is provided an operation program of an information processing apparatus, the program causing a computer to execute: acquiring a medical image showing an organ of a subject and disease-related data of the subject; subdividing the medical image into a plurality of patch images; using a prediction model including a feature amount extraction unit that extracts a feature amount from the patch images and the disease-related data and a correlation information extraction unit that extracts at least correlation information between the plurality of patch images and correlation information between the plurality of patch images and the disease-related data; and inputting the patch images and the disease-related data to the prediction model and outputting a prediction result regarding a disease from the prediction model.

According to the present disclosure, there is provided a prediction model for causing a computer to function to output a prediction result regarding a disease in response to an input of a plurality of patch images obtained by subdividing a medical image showing an organ of a subject and disease-related data of the subject, the prediction model comprising: a feature amount extraction unit that extracts a feature amount from the patch images and the disease-related data; and a correlation information extraction unit that extracts at least correlation information between the plurality of patch images and correlation information between the plurality of patch images and the disease-related data.

According to the present disclosure, there is provided a learning apparatus that provides a prediction model with a learning medical image and a learning disease-related data as learning data, and trains the prediction model to obtain a prediction result regarding a disease as an output in response to an input of a plurality of patch images obtained by subdividing a medical image showing an organ of a subject and disease-related data of the subject, in which the prediction model includes a feature amount extraction unit that extracts a feature amount from the patch images and the disease-related data, and a correlation information extraction unit that extracts at least correlation information between the plurality of patch images and correlation information between the plurality of patch images and the disease-related data.

According to the present disclosure, there is provided a learning method of providing a prediction model with a learning medical image and a learning disease-related data as learning data, and training the prediction model to obtain a prediction result regarding a disease as an output in response to an input of a plurality of patch images obtained by subdividing a medical image showing an organ of a subject and disease-related data of the subject, in which the prediction model includes a feature amount extraction unit that extracts a feature amount from the patch images and the disease-related data, and a correlation information extraction unit that extracts at least correlation information between the plurality of patch images and correlation information between the plurality of patch images and the disease-related data.

According to the technology of the present disclosure, it is possible to provide an information processing apparatus, an operation method of an information processing apparatus, an operation program of an information processing apparatus, a prediction model, a learning apparatus, and a learning method capable of improving a prediction accuracy of a prediction result related to a disease by a prediction model.

BRIEF DESCRIPTION OF THE DRAWINGS

Exemplary embodiments according to the technique of the present disclosure will be described in detail based on the following figures, wherein.

DETAILED DESCRIPTION

First Embodiment

Figure 1:
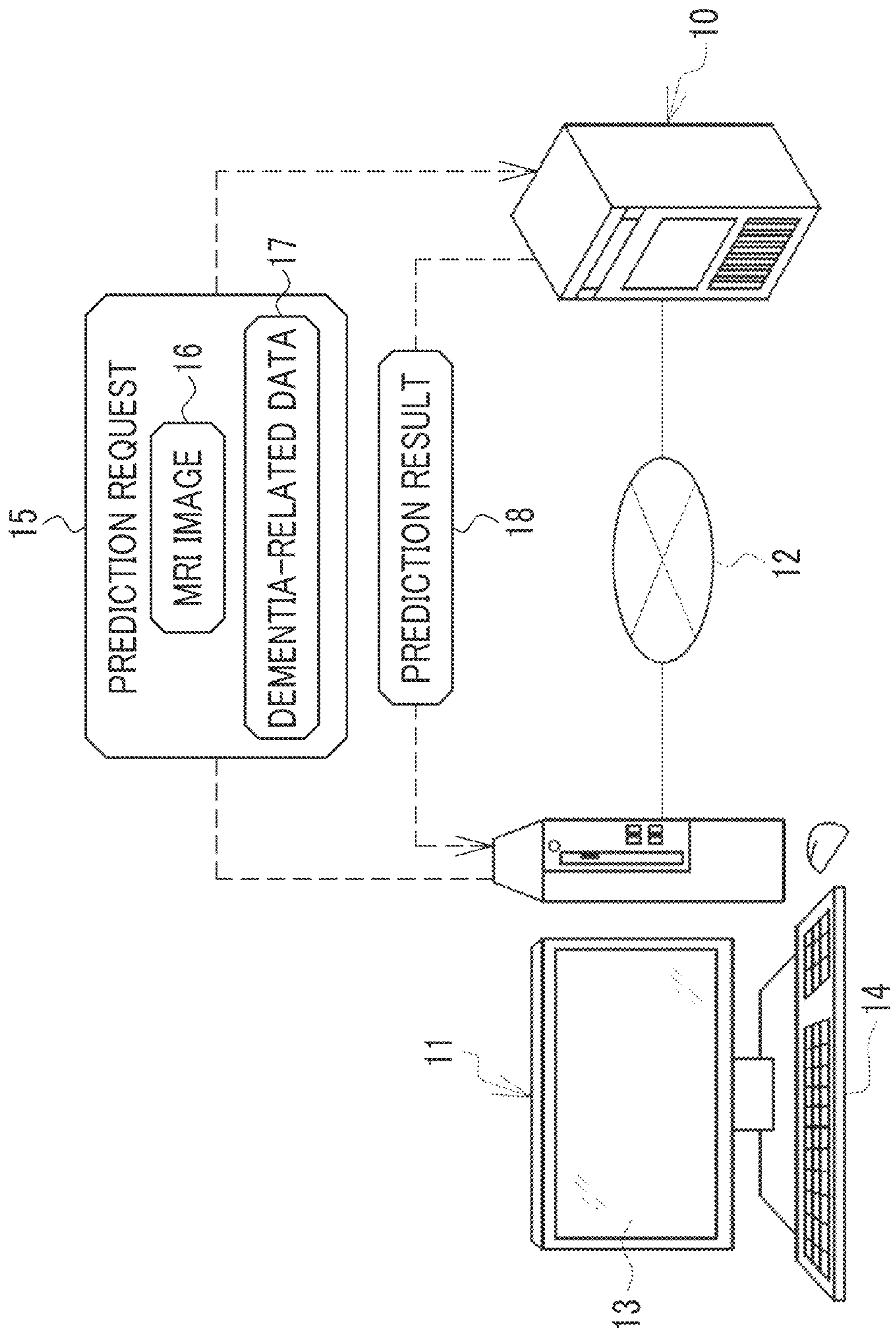
FIG. 1 is a diagram showing an information processing server and a user terminal.

As shown in FIG. 1 as an example, an information processing server 10 is connected to a user terminal 11 via a network 12. The information processing server 10 is an example of an "information processing apparatus" according to the technology of the present disclosure. The user terminal 11 is installed in, for example, a medical facility, and is operated by a doctor who diagnoses dementia, particularly Alzheimer's dementia, at the medical facility.

The dementia is an example of a "disease" according to the technology of the present disclosure. Examples of the dementia include Alzheimer's dementia, Lewy body dementia, and vascular dementia. The content of the diagnosis may be used for Alzheimer's disease other than Alzheimer's dementia. Specifically, examples thereof include a preclinical Alzheimer's disease (PAD) and mild cognitive impairment (MCI) due to Alzheimer's disease. As the disease, a cranial nerve disease such as dementia in the example is preferable.

Diagnostic criteria for the dementia include diagnostic criteria disclosed in "Dementia disease medical care guideline 2017" supervised by the Japanese Society of Neurology, "International Statistical Classification of Diseases and Related Health Problems (ICD)-11", the American Psychiatric Association's "Diagnostic and Statistical Manual of Mental Disorders, Fifth Edition (DSM-5)", and the "National Institute on Aging-Alzheimer's Association workgroup (NIA-AA) criteria". Such diagnostic criteria can be cited, and the contents of which are incorporated in the specification of the present application.

Data related to the diagnostic criteria for the dementia includes cognitive function test data, morphological image test data, brain function image test data, blood/cerebrospinal fluid test data, genetic test data, and the like. The cognitive function test data includes a clinical dementia rating-sum of boxes (hereinafter abbreviated as CDR-SOB) score, a mini-mental state examination (hereinafter abbreviated as MMSE) score, an Alzheimer's disease assessment scale-cognitive subscale (hereinafter abbreviated as ADAS-Cog) score, and the like. The morphological image test data includes an MRI image 16, a brain tomographic image (hereinafter, referred to as a CT image) obtained by computed tomography (CT), or the like.

The brain function image test data includes a brain tomographic image obtained by a positron emission tomography (PET) (hereinafter, referred to as a PET image), a brain tomographic image obtained by a single photon emission computed tomography (SPECT) (hereinafter, referred to as a SPECT image), and the like. The blood/cerebrospinal fluid test data includes an amount of phosphorylated tau protein (p-tau) 181 in cerebrospinal fluid (hereinafter, abbreviated as CSF), and the like. The genetic test data includes a test result of a genotype of an ApoE gene, and the like.

The user terminal 11 includes a display 13 and an input device 14 such as a keyboard and a mouse. The network 12 is, for example, a wide area network (WAN) such as the Internet or a public communication network. In FIG. 1, only one user terminal 11 is connected to the information processing server 10, but in reality, a plurality of the user terminals 11 of a plurality of medical facilities are connected to the information processing server 10.

The user terminal 11 transmits a prediction request 15 to the information processing server 10. The prediction request 15 is a request for causing the information processing server 10 to predict progression of the dementia using a prediction model 41 (see FIG. 5). The prediction request 15 includes the MRI image 16 and dementia-related data 17. The MRI image 16 and the dementia-related data 17 are data on the transmission date of the prediction request 15. The MRI image 16 and the dementia-related data 17 may be data most recent to the transmission date of the prediction request 15, for example, data from 3 days before to 1 week before the transmission date of the prediction request 15.

The MRI image 16 is an image showing a brain of a subject for which progression of dementia is to be predicted. The MRI image 16 is voxel data representing a three-dimensional shape of the brain of the subject (see FIG. 6). The MRI image 16 is an example of a "medical image" and "morphological image test data" according to the technology of the present disclosure. In addition, the brain is an example of an "organ" according to the technology of the present disclosure.

The dementia-related data 17 is data related to the dementia of the subject. The MRI image 16 is obtained from, for example, a picture archiving and communication system (PACS) server. The dementia-related data 17 is obtained from, for example, an electronic medical record server. Alternatively, the dementia-related data 17 is input by the doctor operating the input device 14. The dementia-related data 17 is an example of "disease-related data" according to the technology of the present disclosure. Although not shown, the prediction request 15 also includes a terminal identification data (ID) or the like for uniquely identifying the user terminal 11 which is a transmission source of the prediction request 15.

In a case where the prediction request 15 is received, the information processing server 10 uses the prediction model 41 to predict the progression of the dementia of the subject, and derives a prediction result 18. The information processing server 10 distributes the prediction result 18 to the user terminal 11 which is a transmission source of the prediction request 15. In a case where the prediction result 18 is received, the user terminal 11 displays the prediction result 18 on the display 13 and makes the prediction result 18 available for viewing by the doctor.

Figure 2:
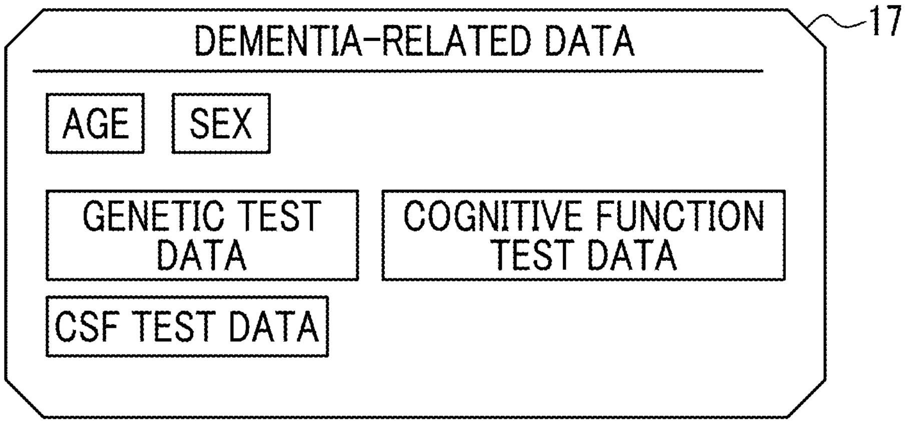
FIG. 2 is a diagram showing dementia-related data.

As shown in FIG. 2 as an example, the dementia-related data 17 includes an age, a sex, genetic test data, cognitive function test data, and CSF test data of the subject. The genetic test data is, for example, a test result of a genotype of an ApoE gene. The genotype of the ApoE gene is a combination of two types among three types of ApoE genes of ε2, ε3, and ε4 (ε2 and ε3, ε3 and ε4, and the like). A risk of developing Alzheimer's dementia in a subject with a genotype including one or two of ε4 (ε2 and ε4, ε4 and ε4, and the like) is estimated to be about 3 to 12 times higher than that in a subject with a genotype without ε4 (ε2 and ε3, ε3 and ε3, and the like). The cognitive function test data is, for example, a score of the CDR-SOB. The CSF test data is, for example, an amount of phosphorylated tau protein (p-tau) 181 in CSF. The CSF test data is an example of "blood/cerebrospinal fluid test data" according to the technology of the present disclosure.

Figure 3:
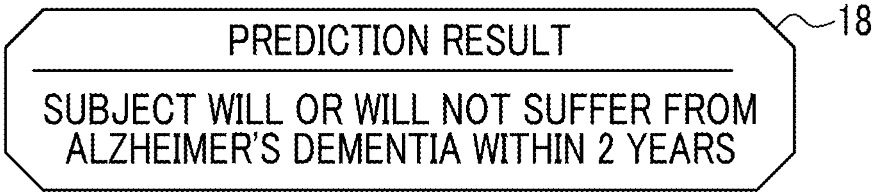
FIG. 3 is a diagram showing a prediction result.

As shown in FIG. 3 as an example, the prediction result 18 is the content indicating whether the subject will or will not suffer from Alzheimer's dementia within 2 years.

Figure 4:
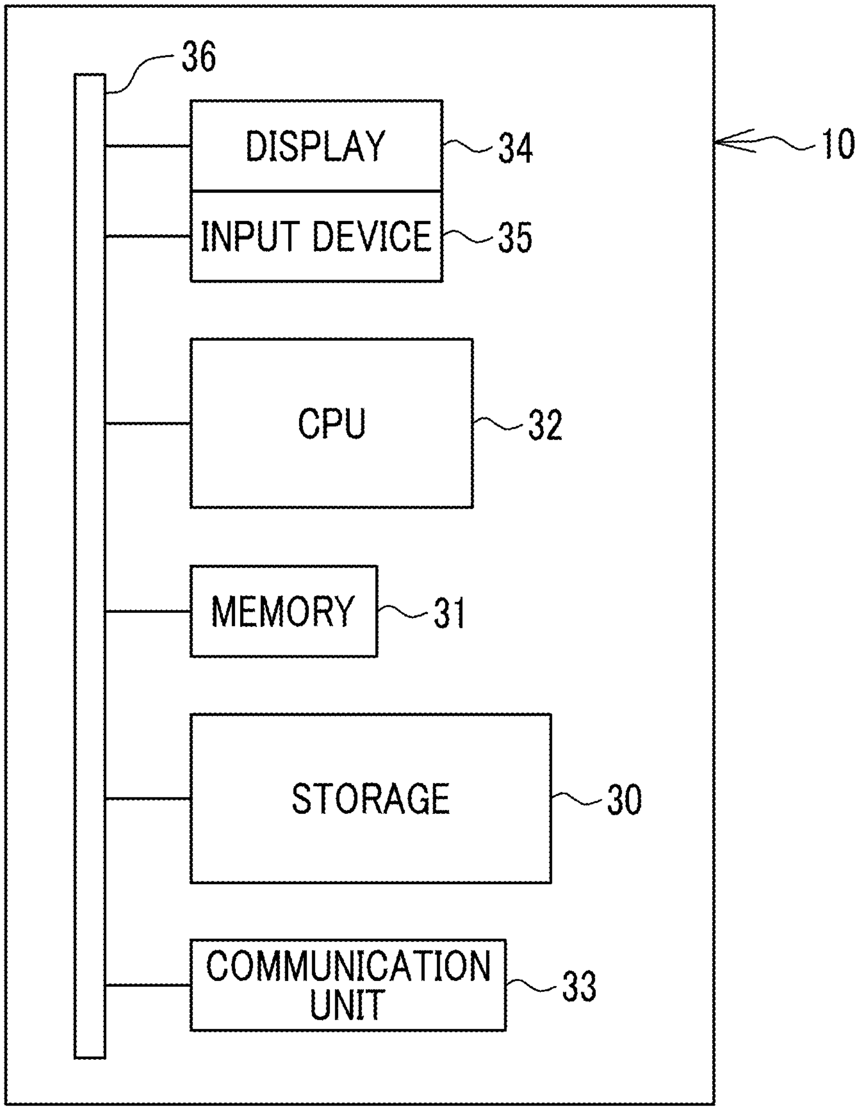
FIG. 4 is a block diagram showing a computer constituting the information processing server.

As shown in FIG. 4 as an example, a computer constituting the information processing server 10 comprises a storage 30, a memory 31, a central processing unit (CPU) 32, a communication unit 33, a display 34, and an input device 35. These units are connected to each other via a bus line 36.

The storage 30 is a hard disk drive that is built in the computer constituting the information processing server 10 or that is connected to the computer through a cable or the network. Alternatively, the storage 30 is a disk array in which a plurality of hard disk drives are continuously mounted. The storage 30 stores a control program such as an operating system, various types of application programs, and various types of data associated with these programs. A solid state drive may be used instead of the hard disk drive.

The memory 31 is a work memory for the CPU 32 to perform processing. The CPU 32 loads the program stored in the storage 30 into the memory 31 and executes processing corresponding to the program. Thus, the CPU 32 collectively controls the respective units of the computer. The CPU 32 is an example of a "processor" according to the technology of the present disclosure. The memory 31 may be built in the CPU 32.

The communication unit 33 controls transmission of various types of information to an external device such as the user terminal 11. The display 34 displays various screens. The various screens have operation functions by a graphical user interface (GUI). The computer constituting the information processing server 10 receives an input of an operation instruction from the input device 35 through the various screens. The input device 35 is a keyboard, a mouse, a touch panel, a microphone for voice input, or the like.

Figure 5:
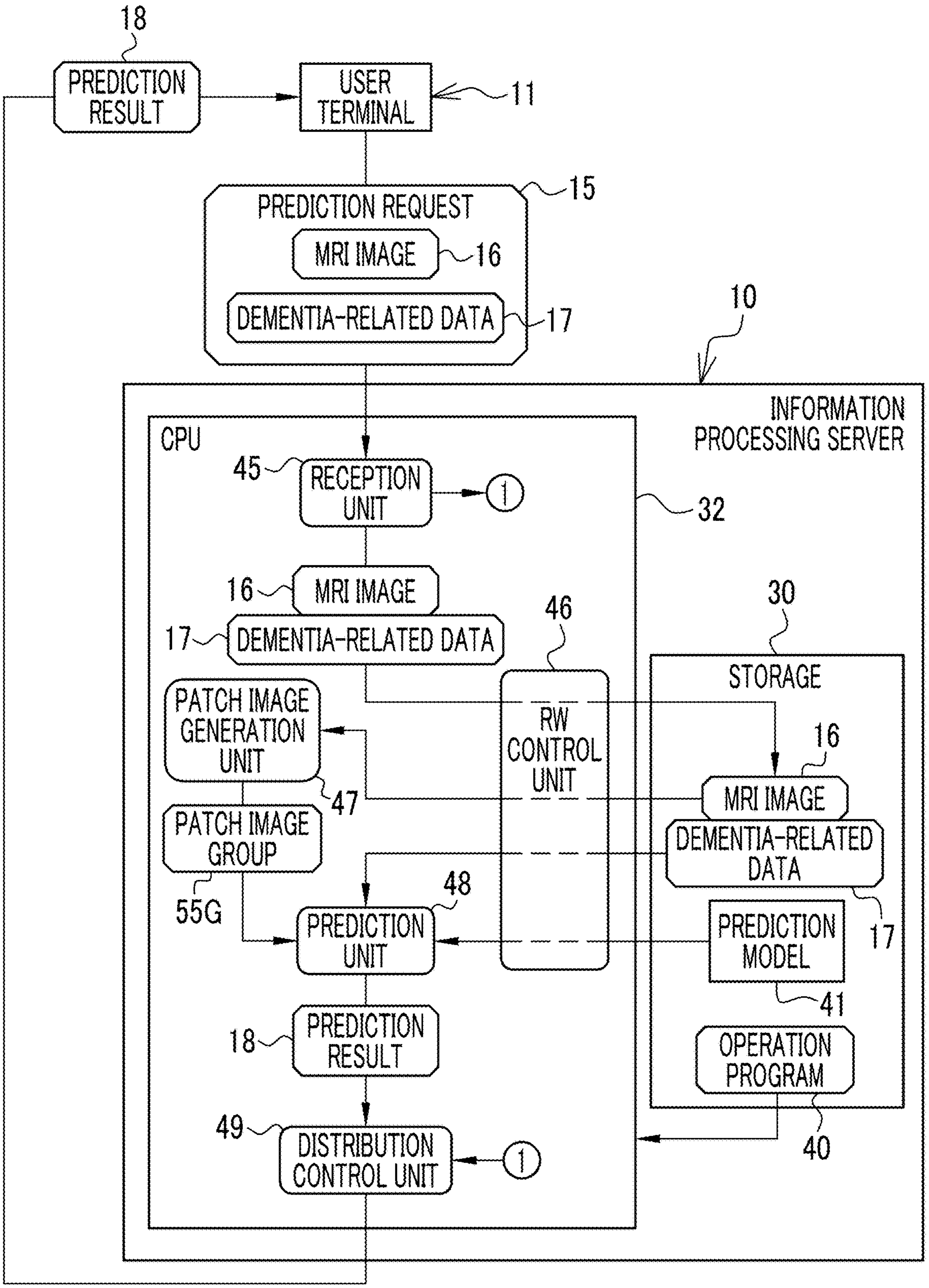
FIG. 5 is a block diagram showing a processing unit of a CPU of the information processing server.

As shown in FIG. 5 as an example, an operation program 40 is stored in the storage 30 of the information processing server 10. The operation program 40 is an application program for causing the computer to function as the information processing server 10. That is, the operation program 40 is an example of an "operation program of an information processing apparatus" according to the technology of the present disclosure. The storage 30 also stores the prediction model 41.

In a case where the operation program 40 is activated, the CPU 32 of the computer constituting the information processing server 10 functions as a reception unit 45, a read write (hereinafter, abbreviated as RW) control unit 46, a patch image generation unit 47, a prediction unit 48, and a distribution control unit 49 in cooperation with the memory 31 and the like.

The reception unit 45 receives the prediction request 15 from the user terminal 11. The prediction request 15 includes the MRI image 16 and the dementia-related data 17 as described above. Therefore, the reception unit 45 acquires the MRI image 16 and the dementia-related data 17 by receiving the prediction request 15. The reception unit 45 outputs the acquired MRI image 16 and the acquired dementia-related data 17 to the RW control unit 46. In addition, the reception unit 45 outputs a terminal ID of the user terminal 11 (not shown) to the distribution control unit 49.

The RW control unit 46 controls storage of various types of data in the storage 30 and reading out of various types of data in the storage 30. For example, the RW control unit 46 stores the MRI image 16 and the dementia-related data 17 from the reception unit 45 in the storage 30. In addition, the RW control unit 46 reads out the MRI image 16 and the dementia-related data 17 from the storage 30, outputs the MRI image 16 to the patch image generation unit 47, and outputs the dementia-related data 17 to the prediction unit 48. Further, the RW control unit 46 reads out the prediction model 41 from the storage 30, and outputs the prediction model 41 to the prediction unit 48.

Figure 6:
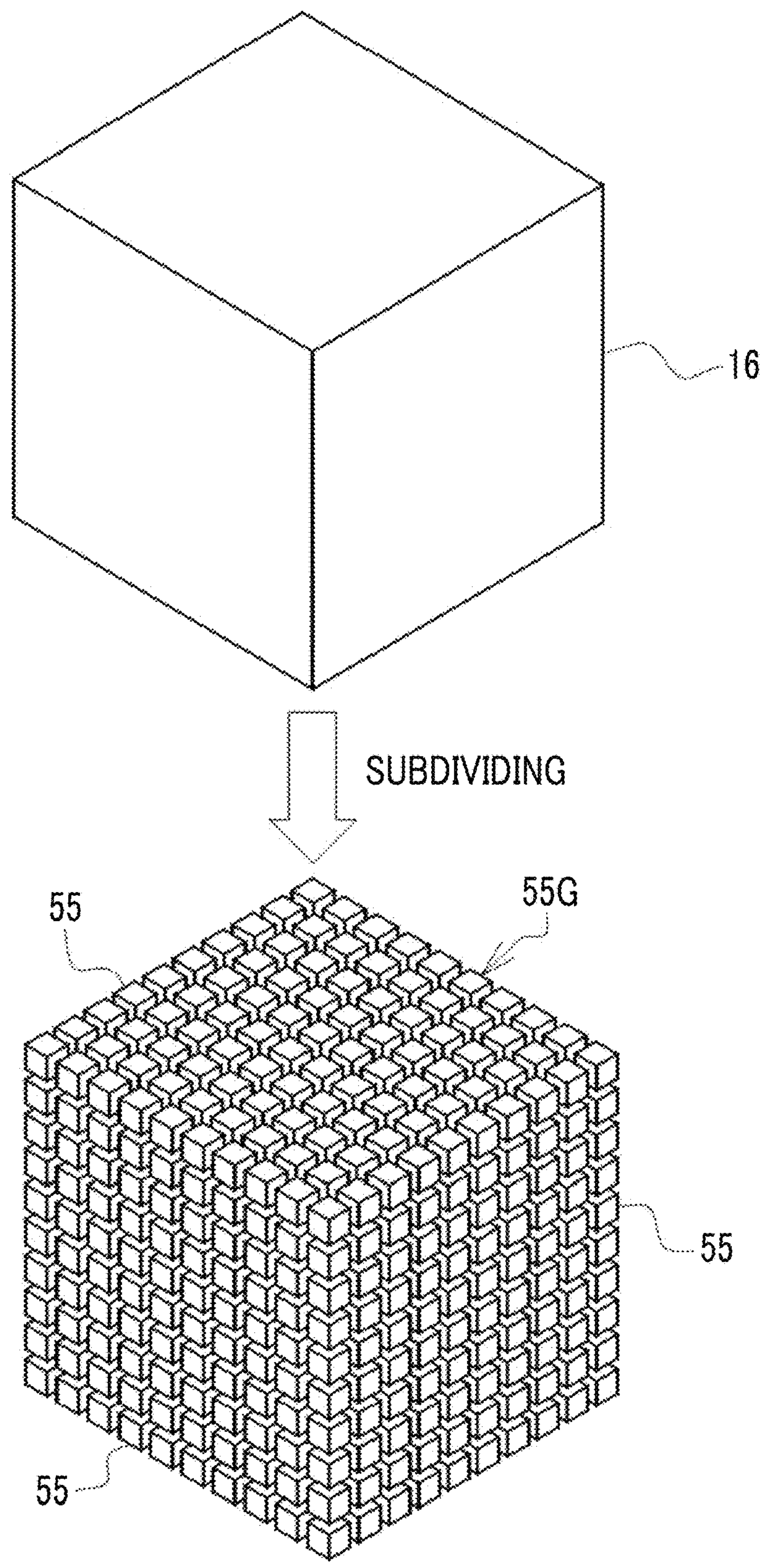
FIG. 6 is a diagram conceptually showing processing of a patch image generation unit.

As shown in FIG. 6 as an example, the patch image generation unit 47 subdivides the MRI image 16 into a plurality of patch images 55. The patch image 55 has, for example, a size of 8 pixels×8 pixels×8 pixels. The patch image generation unit 47 outputs a patch image group 55G, which is a set of the plurality of patch images 55, to the prediction unit 48.

The prediction unit 48 inputs the patch image group 55G and the dementia-related data 17 to the prediction model 41, and causes the prediction model 41 to output the prediction result 18. The prediction unit 48 outputs the prediction result 18 to the distribution control unit 49.

The distribution control unit 49 performs control to distribute the prediction result 18 to the user terminal 11 which is a transmission source of the prediction request 15. In this case, the distribution control unit 49 specifies the user terminal 11, which is the transmission source of the prediction request 15, based on the terminal ID from the reception unit 45.

Figure 7:
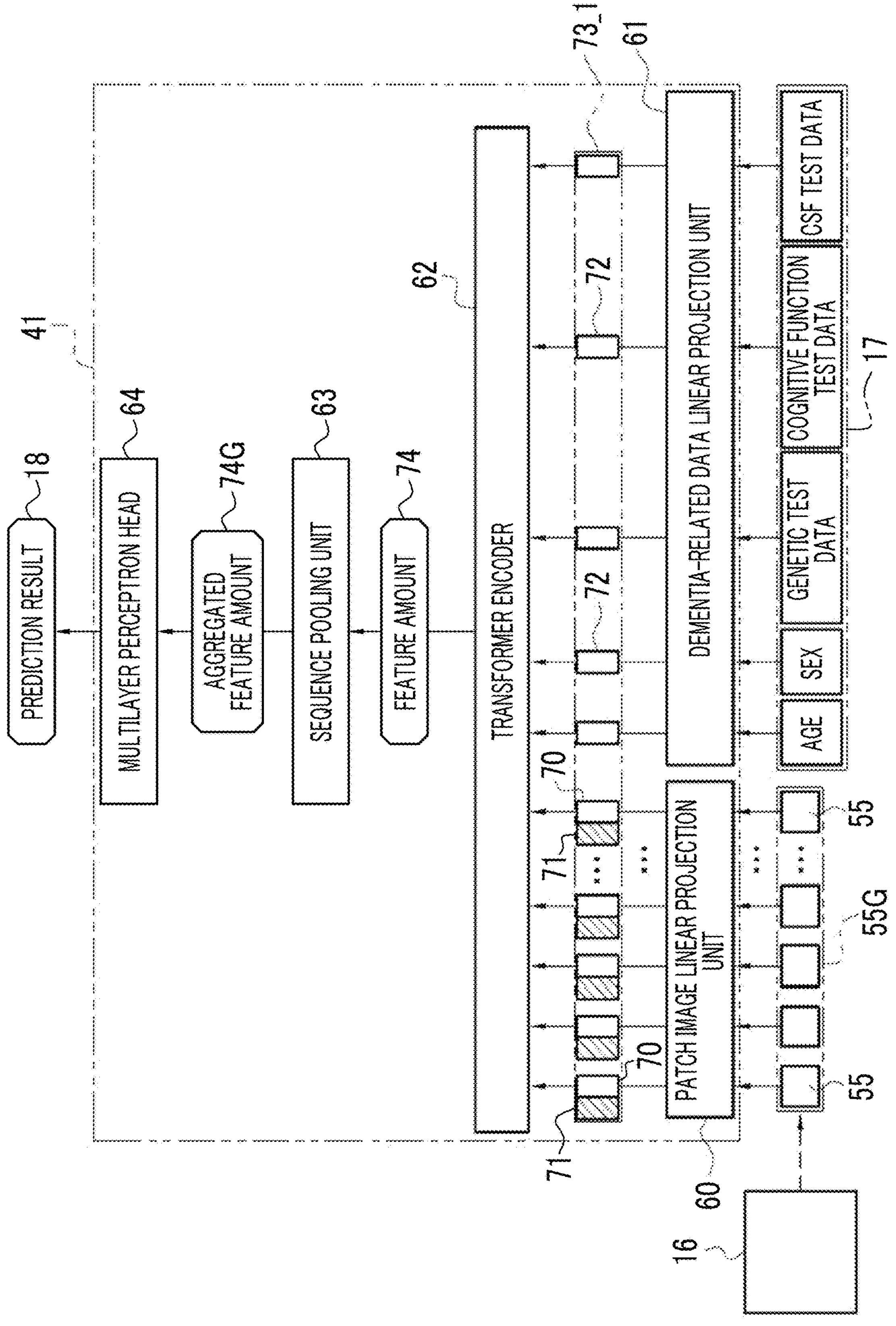
FIG. 7 is a block diagram showing a detailed configuration of a prediction model.

As shown in FIG. 7 as an example, the prediction model 41 includes a patch image linear projection unit 60, a dementia-related data linear projection unit 61, a transformer encoder 62, a sequence pooling unit 63, and a multilayer perceptron (MLP) head 64. The patch image linear projection unit 60 converts each of the plurality of patch images 55 constituting the patch image group 55G into sequence data, and then linearly projects the sequence data. Specifically, the patch image linear projection unit 60 first converts each patch image 55 into a one-dimensional vector. Then, each one-dimensional patch image 55 is linearly projected onto a multi-dimensional, for example, 64-dimensional tensor through a filter. The filter that performs the linear projection is trained in a learning phase of the prediction model 41 (see FIG. 10). The patch image linear projection unit 60 outputs a plurality of pieces of tensor data (referred to as patch embedding) 70 obtained by linearly projecting each patch image 55 to the transformer encoder 62. In this case, position information 71 is assigned to the tensor data 70 (referred to as position embedding). The position information 71 is information for identifying a position of the patch image 55 in the MRI image 16.

The dementia-related data linear projection unit 61 converts each of the age, the sex, the genetic test data, the cognitive function test data, and the CSF test data of the subject constituting the dementia-related data 17 into the sequence data, and then linearly projects the sequence data. Specifically, the dementia-related data linear projection unit 61 first converts each piece of the dementia-related data 17 into a one-dimensional vector. Then, each piece of the one-dimensional dementia-related data 17 is linearly projected onto a multi-dimensional, for example, 64-dimensional tensor through a filter. As in the case of the patch image linear projection unit 60, the filter that performs the linear projection is trained in the learning phase of the prediction model 41. The dementia-related data linear projection unit 61 outputs tensor data 72 obtained by linearly projecting each piece of the dementia-related data 17 to the transformer encoder 62. That is, the tensor data 70 based on the patch image 55 and the tensor data 72 based on the dementia-related data 17 are simultaneously input to the transformer encoder 62. Hereinafter, a set of the tensor data 70, the position information 71, and the tensor data 72 is referred to as first input data 73_1. The first input data 73_1 is an example of "input data in which the patch images and the dementia-related data are mixed" according to the technology of the present disclosure.

The transformer encoder 62 extracts a feature amount 74 from the first input data 73_1. The feature amount 74 is a set of a plurality of, for example, thousands to hundreds of thousands of numerical values. The transformer encoder 62 outputs the feature amount 74 to the sequence pooling unit 63. The transformer encoder 62 is trained in the learning phase of the prediction model 41.

The sequence pooling unit 63 obtains a statistical value of the feature amount 74, here, an average value, and outputs the obtained average value to the multilayer perceptron head 64 as an aggregated feature amount 74G. The statistic value is not limited to the average value, and may be a maximum value or the like.

The multilayer perceptron head 64 converts the aggregated feature amount 74G into the prediction result 18. The multilayer perceptron head 64 is trained in the learning phase of the prediction model 41.

Figure 8:
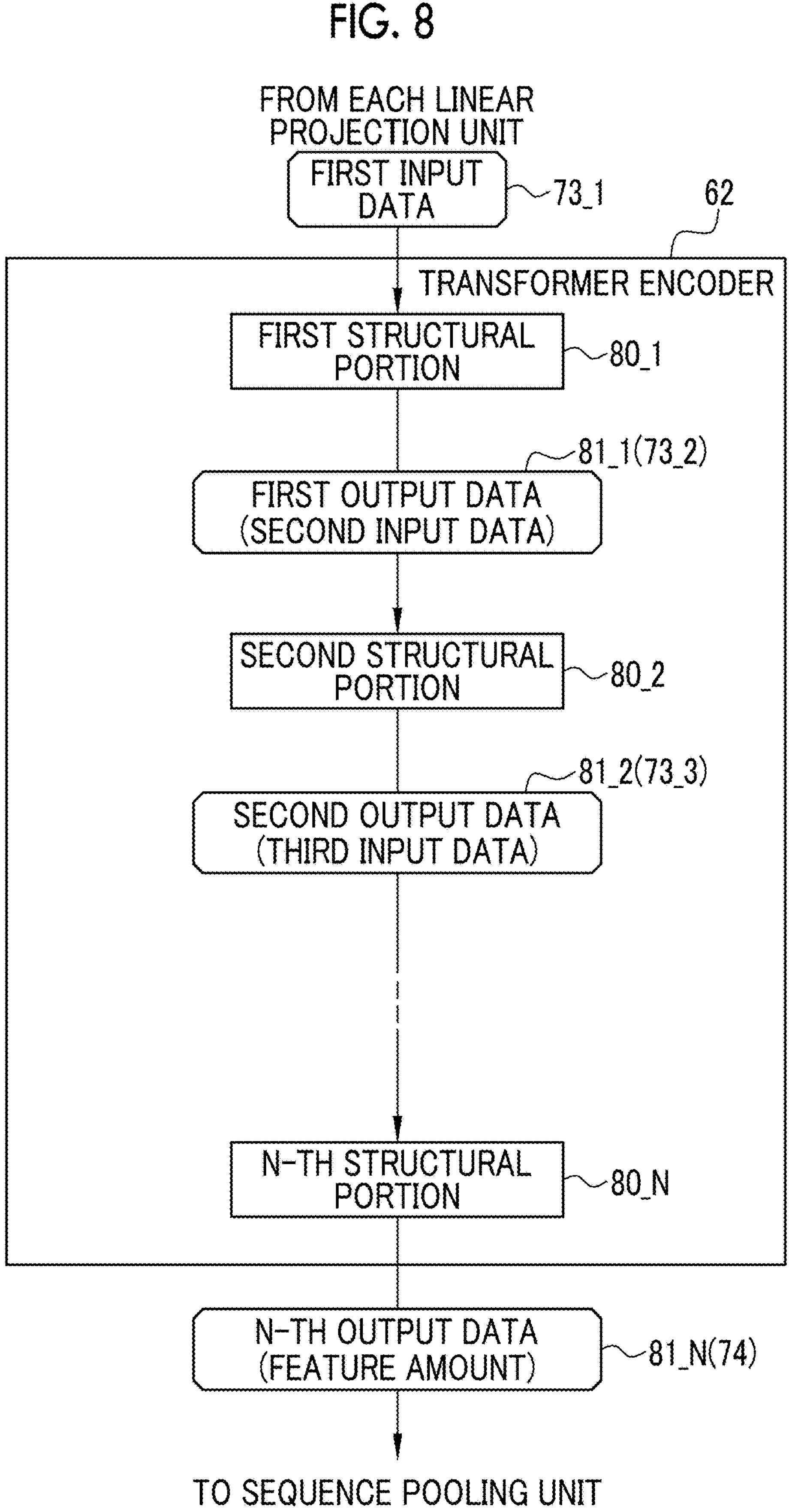
FIG. 8 is a diagram showing a detailed configuration of a transformer encoder.

As shown in FIG. 8 as an example, the transformer encoder 62 includes a plurality of structural portions 80, that is, a first structural portion 80_1, a second structural portion 80_2, . . . , and an N-th structural portion 80_N (N is a natural number of 2 or more). The plurality of structural portions 80 have the same structure.

The first input data 73_1 is input to the first structural portion 80_1. The first structural portion 80_1 outputs first output data 81_1 based on the first input data 73_1. The first output data 81_1 is input to the second structural portion 80_2. That is, the first output data 81_1 is also second input data 73_2 of the second structural portion 802. The second structural portion 80_2 outputs second output data 81_2 based on the second input data 73_2. The second output data 812 is input to a third structural portion (not shown). That is, the second output data 81_2 is also third input data 73_3 of the third structural portion. In this way, a process in which the output data 81 of the structural portion 80 in the preceding stage is input to the structural portion 80 in the subsequent stage as the input data 73 is repeatedly performed. Then, finally, the N-th output data 81_N is output from the N-th structural portion 80_N. The N-th output data 81_N is nothing but the feature amount 74 that is a final output of the transformer encoder 62.

Figure 9:
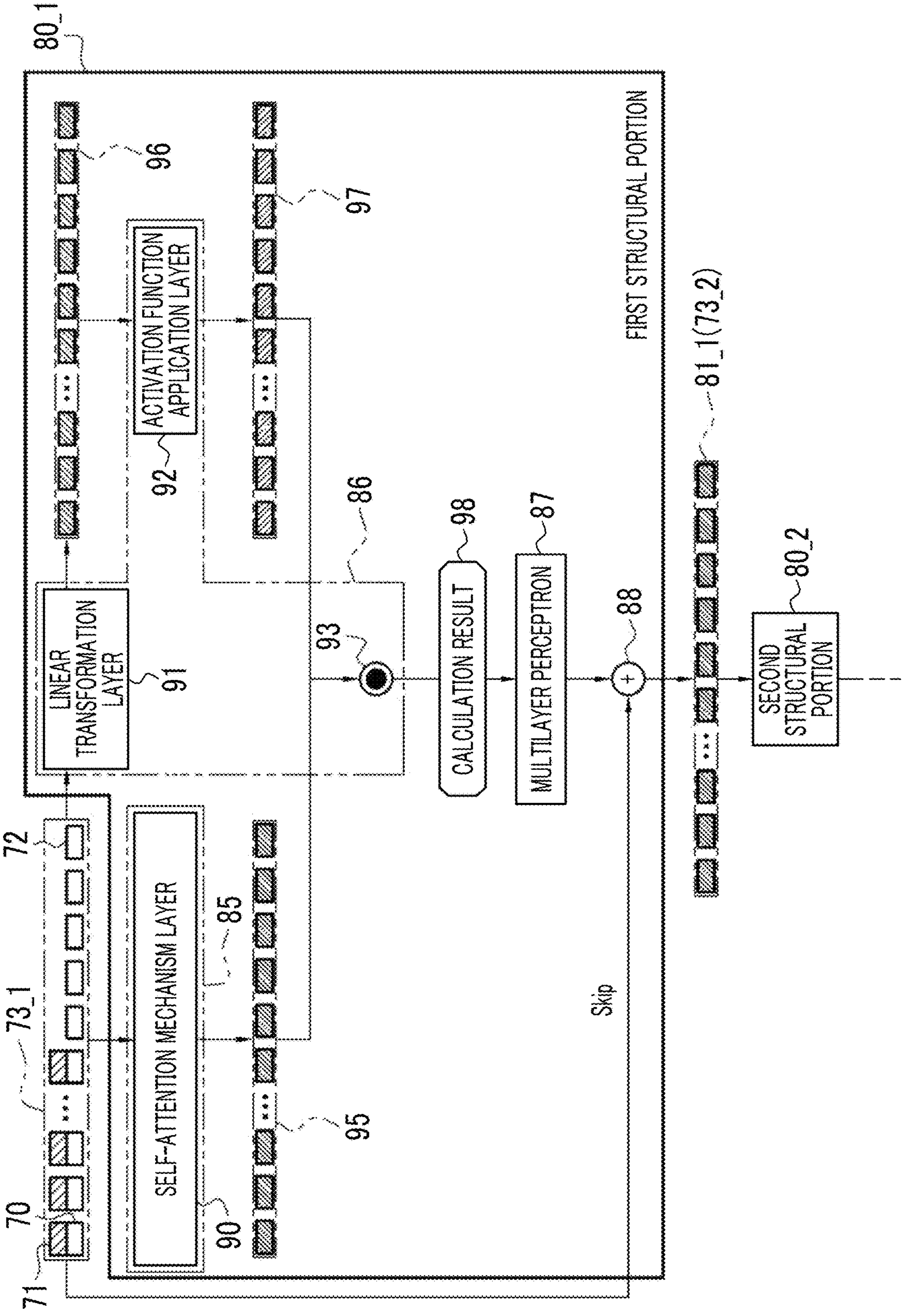
FIG. 9 is a diagram showing a detailed configuration of a first structural portion.

As shown in FIG. 9 as an example, the first structural portion 80_1 includes a feature amount extraction unit 85, a correlation information extraction unit 86, a multilayer perceptron 87, and an addition unit 88. The feature amount extraction unit 85 includes a self-attention mechanism layer 90. The correlation information extraction unit 86 includes a linear transformation layer 91, an activation function application layer 92, and a calculation unit 93. As described above, since the other structural portions 80 also have the same structure as the first structural portion 80_1, the first structural portion 80_1 will be described below as a representative.

The first input data 73_1 is input to the self-attention mechanism layer 90. As is well known, the self-attention mechanism layer 90 acquires a query, a key, and a value of each piece of the tensor data 70 and the tensor data 72 of the first input data 73_1, and calculates a degree of similarity between the query and the key. As a result, the self-attention mechanism layer 90 generates an attention weight map indicating a correspondence relationship between each patch image 55 and the dementia-related data 17. The attention weight map is a set of numerical values between 0 and 1, which represent which of the first input data 73_1 should be noticed. The self-attention mechanism layer 90 treats the numerical value of the attention weight map as a probability, and computes a correspondence relationship between the query and the value, thereby making the first input data 73_1 as intermediate output data 95. The self-attention mechanism layer 90 outputs the intermediate output data 95 to the calculation unit 93. The intermediate output data 95 is an example of "output data from the self-attention mechanism layer" according to the technology of the present disclosure.

The first input data 73_1 is also input to the linear transformation layer 91. The linear transformation layer 91 linearly transforms the first input data 73_1 to obtain first transformation data 96. The linear transformation layer 91 outputs the first transformation data 96 to the activation function application layer 92.

The activation function application layer 92 applies an activation function such as a sigmoid function to the first transformation data 96 to obtain second transformation data 97. The activation function application layer 92 outputs the second transformation data 97 to the calculation unit 93.

The calculation unit 93 calculates a product of the intermediate output data 95 from the self-attention mechanism layer 90 and the second transformation data 97 from the activation function application layer 92 for each element. A calculation result 98 of the product between the intermediate output data 95 and the second transformation data 97 for each element is correlation information between the plurality of patch images 55, correlation information between the plurality of patch images 55 and each piece of the dementia-related data 17, and correlation information between pieces of the dementia-related data 17. The calculation unit 93 outputs the calculation result 98 to the multilayer perceptron 87.

The multilayer perceptron 87 linearly transforms the calculation result 98 and outputs the linearly transformed calculation result 98 to the addition unit 88. The addition unit 88 adds the first input data 73_1 and the calculation result 98 after the linear transformation to obtain first output data 81_1. As described above, the first output data 81_1 is input to the second structural portion 80_2 as the second input data 73_2.

As described above, the prediction model 41 causes the computer to function to execute feature amount extraction processing via the feature amount extraction unit 85 for extracting the feature amount 74 from the plurality of patch images 55 obtained by subdividing the MRI image 16 showing the brain of the subject and the dementia-related data 17 of the subject, correlation information extraction processing via the correlation information extraction unit 86 for extracting the calculation result 98 as the correlation information between the plurality of patch images 55 and the correlation information between the plurality of patch images 55 and the dementia-related data 17, and prediction result output processing via the multilayer perceptron head 64 for outputting the prediction result 18 related to the dementia in response to the input of the patch images 55 and the dementia-related data 17.

Figure 10:
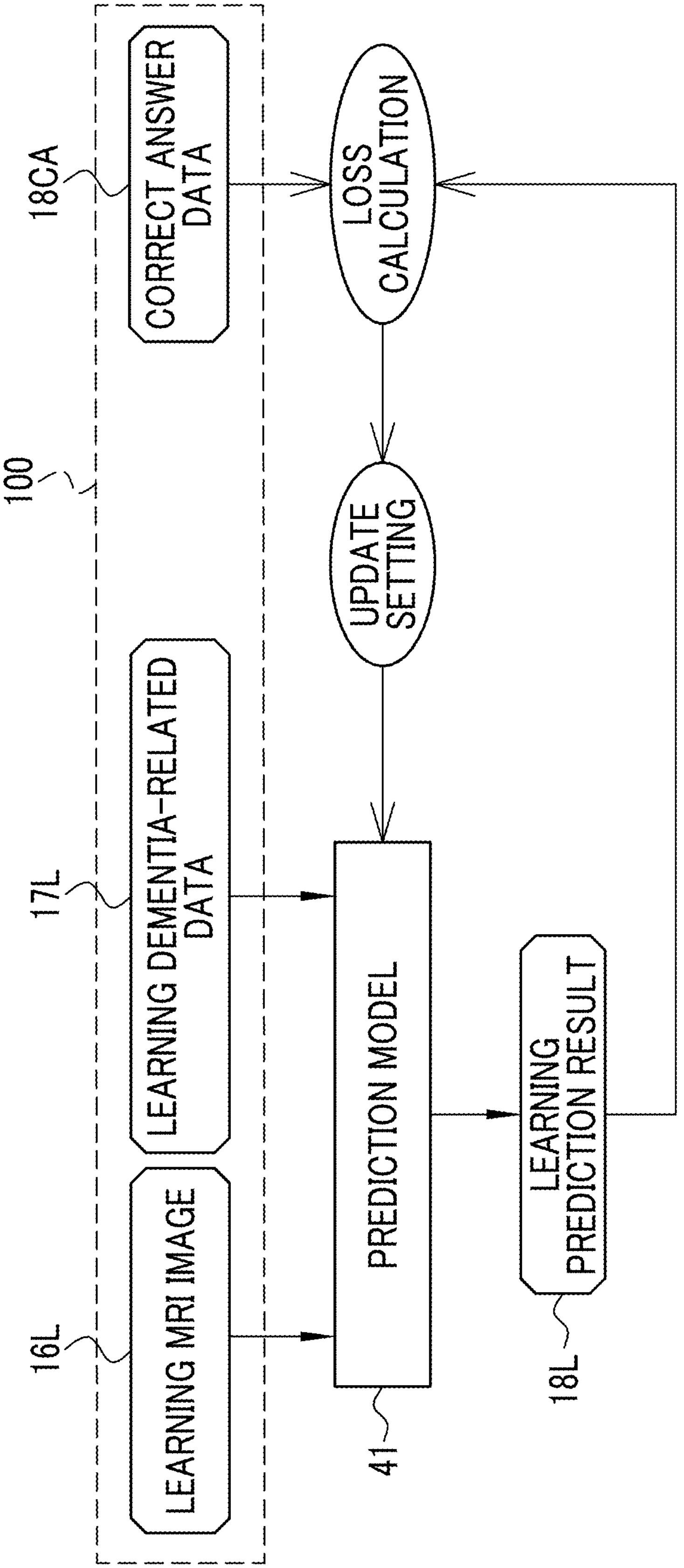
FIG. 10 is a diagram showing an outline of processing in a learning phase of the prediction model.

As shown in FIG. 10 as an example, the prediction model 41 is trained by being given learning data (also referred to as teaching data or learning data) 100 in the learning phase. The learning data 100 is a set of a learning MRI image 16L, learning dementia-related data 17L, and correct answer data 18CA. The learning MRI image 16L and the learning dementia-related data 17L are the MRI image 16 and the dementia-related data 17 of a certain sample subject (including a patient), which are accumulated in a database such as Alzheimer's Disease Neuroimaging Initiative (ADNI). The correct answer data 18CA is an actual diagnosis result of Alzheimer's dementia given by the doctor to the sample subject.

In the learning phase, the learning MRI image 16L and the learning dementia-related data 17L are input to the prediction model 41. The prediction model 41 outputs a learning prediction result 18L for the learning MRI image 16L and the learning dementia-related data 17L. Loss calculation of the prediction model 41 is performed based on the learning prediction result 18L and the correct answer data 18CA. Then, update setting of various coefficients of the prediction model 41 is performed according to a result of the loss calculation, and the prediction model 41 is updated in accordance with the update setting.

In the learning phase, while exchanging the learning data 100 at least two or more times, a series of processing including inputting of the learning MRI image 16L and the learning dementia-related data 17L to the prediction model 41, outputting of the learning prediction result 18L from the prediction model 41, the loss calculation, the update setting, and updating of the prediction model 41 is repeatedly performed. The repetition of the series of processing is ended in a case where a prediction accuracy of the learning prediction result 18L with respect to the correct answer data 18CA has reached a predetermined set level. The prediction model 41 of which the prediction accuracy has reached the set level in this way is stored in the storage 30, and is used in the prediction unit 48. The learning may be ended in a case where the above-described series of processing is repeated a set number of times, regardless of the prediction accuracy of the learning prediction result 18L for the correct answer data 18CA.

Figure 11:
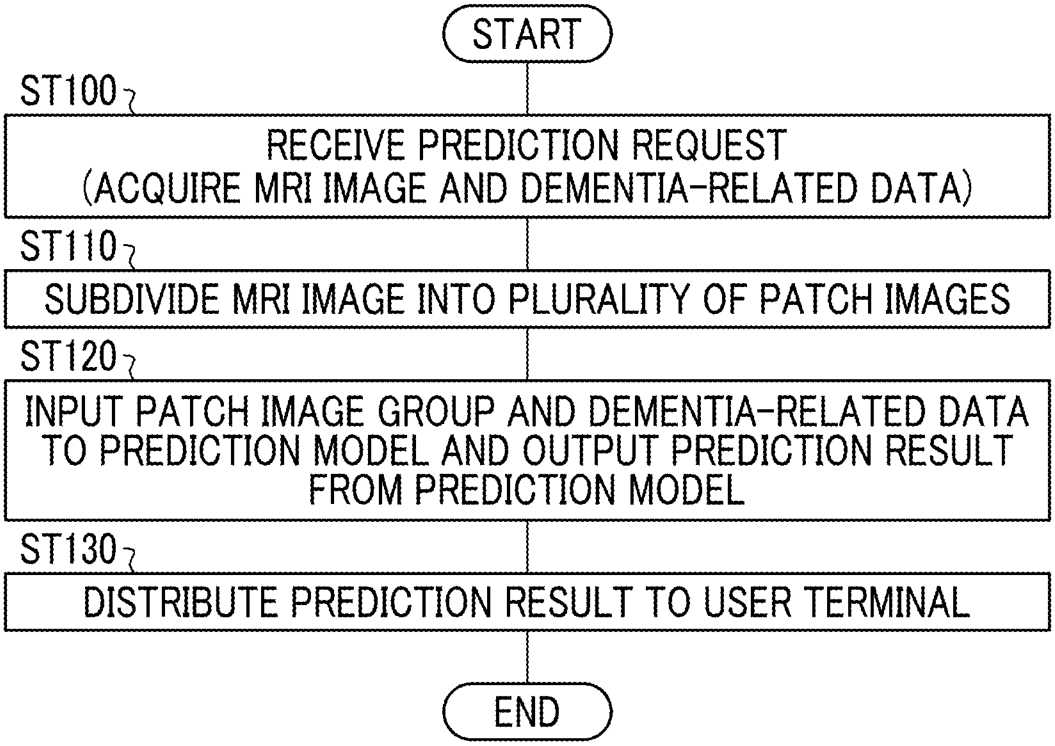
FIG. 11 is a flowchart showing a procedure of processing of the information processing server.

Next, an operation according to the configuration will be described with reference to a flowchart in FIG. 11. First, in a case where the operation program 40 is activated in the information processing server 10, as shown in FIG. 5, the CPU 32 of the information processing server 10 functions as the reception unit 45, the RW control unit 46, the patch image generation unit 47, the prediction unit 48, and the distribution control unit 49.

First, the reception unit 45 receives the prediction request 15 from the user terminal 11 to acquire the MRI image 16 and the dementia-related data 17 (step ST100). The MRI image 16 and the dementia-related data 17 are output from the reception unit 45 to the RW control unit 46 and are stored in the storage 30 under the control of the RW control unit 46.

The MRI image 16 and the dementia-related data 17 are read out from the storage 30 by the RW control unit 46. The MRI image 16 is output from the RW control unit 46 to the patch image generation unit 47. The dementia-related data 17 is output from the RW control unit 46 to the prediction unit 48.

As shown in FIG. 6, in the patch image generation unit 47, the MRI image 16 is subdivided into the plurality of patch images 55 (step ST110). The patch image group 55G, which is a set of the plurality of patch images 55, is output from the patch image generation unit 47 to the prediction unit 48.

As shown in FIG. 7, in the prediction unit 48, the patch image group 55G and the dementia-related data 17 are input to the prediction model 41, and the prediction result 18 is output from the prediction model 41 (step ST120). The prediction result 18 is output from the prediction unit 48 to the distribution control unit 49, and is distributed to the user terminal 11 which is the transmission source of the prediction request 15 under the control of the distribution control unit 49 (step ST130). In the user terminal 11, the prediction result 18 is displayed on the display 13, and the prediction result 18 is made available for viewing by the doctor.

As described above, the CPU 32 of the information processing server 10 comprises the reception unit 45, the patch image generation unit 47, and the prediction unit 48. The reception unit 45 receives the prediction request 15, thereby acquiring the MRI image 16 showing the brain of the subject for which the progression of the dementia is to be predicted and the dementia-related data 17 regarding the dementia of the subject. The patch image generation unit 47 subdivides the MRI image 16 into the plurality of patch images 55. The prediction unit 48 uses the prediction model 41 including the feature amount extraction unit 85 and the correlation information extraction unit 86. The feature amount extraction unit 85 extracts the feature amount 74 from the patch images 55 and the dementia-related data 17. The correlation information extraction unit 86 extracts the calculation result 98 as the correlation information between the plurality of patch images 55 and the correlation information between the plurality of patch images 55 and each piece of the dementia-related data 17. The prediction unit 48 inputs the patch images 55 and the dementia-related data 17 to the prediction model 41, and causes the prediction model 41 to output the prediction result 18 for the progression of the dementia. The correlation information between the plurality of patch images 55 and the correlation information between the plurality of patch images 55 and each piece of the dementia-related data 17 can be effectively used for predicting the progression of the dementia. Therefore, it is possible to increase the prediction accuracy of the prediction result 18 related to the dementia by the prediction model 41.

The transformer encoder is a model that has achieved the state of the art (SOA) in various fields of natural language processing, and has recently been applied to image processing as well as natural language processing. The transformer encoder applied to the image processing is called a vision transformer (ViT) encoder. The vision transformer encoder treats patch images obtained by subdividing an image in the same manner as words in natural language processing. The vision transformer encoder can significantly reduce a computational cost in learning as compared with a model in the related art using, for example, a convolutional neural network, and has a higher prediction accuracy than the model in the related art. In the technology of the present disclosure, the transformer encoder 62 having the mechanism of the vision transformer encoder takes in the first input data 73_1 in which the patch images 55 and the dementia-related data 17 are mixed, the transformer encoder 62 extracts the feature amount 74. Therefore, it is possible to perform learning using a larger amount of learning data 100 in a short time, and it is possible to further increase the prediction accuracy of the prediction result 18 related to the dementia by the prediction model 41.

The feature amount extraction unit 85 includes the self-attention mechanism layer 90 of the transformer encoder 62. In addition, the correlation information extraction unit 86 includes the linear transformation layer 91, the activation function application layer 92, and the calculation unit 93. The linear transformation layer 91 linearly transforms the input data 73 to the self-attention mechanism layer 90 to obtain the first transformation data 96. The activation function application layer 92 applies an activation function to the first transformation data 96 to obtain the second transformation data 97. The calculation unit 93 calculates a product of the intermediate output data 95 from the self-attention mechanism layer 90 and the second transformation data 97 for each element. Therefore, it is possible to easily obtain the calculation result 98 as the correlation information between the plurality of patch images 55, the correlation information between the plurality of patch images 55 and each piece of the dementia-related data 17, and the correlation information between pieces of the dementia-related data 17.

The morphological image test data such as the MRI image 16 is captured for almost all the dementia subjects. Therefore, in a case where the medical image is used as the morphological image test data such as the MRI image 16, there is no shortage of the learning data 100 of the prediction model 41, and the learning of the prediction model 41 proceeds.

The progression of the dementia varies depending on the age, the sex, the blood/cerebrospinal fluid test data (in the present example, CSF test data), and the genetic test data. In addition, the cognitive function test data is a good indicator for predicting the progression of the dementia. Therefore, in a case where the age, the sex, the blood/cerebrospinal fluid test data, the genetic test data, and the cognitive function test data of the subject are included in the dementia-related data 17, the prediction accuracy of the prediction result 18 related to the dementia by the prediction model 41 can be further increased. The dementia-related data 17 need only include at least one of the age, the sex, the blood/cerebrospinal fluid test data, the genetic test data, or the cognitive function test data of the subject.

Second Embodiment

Figure 12:
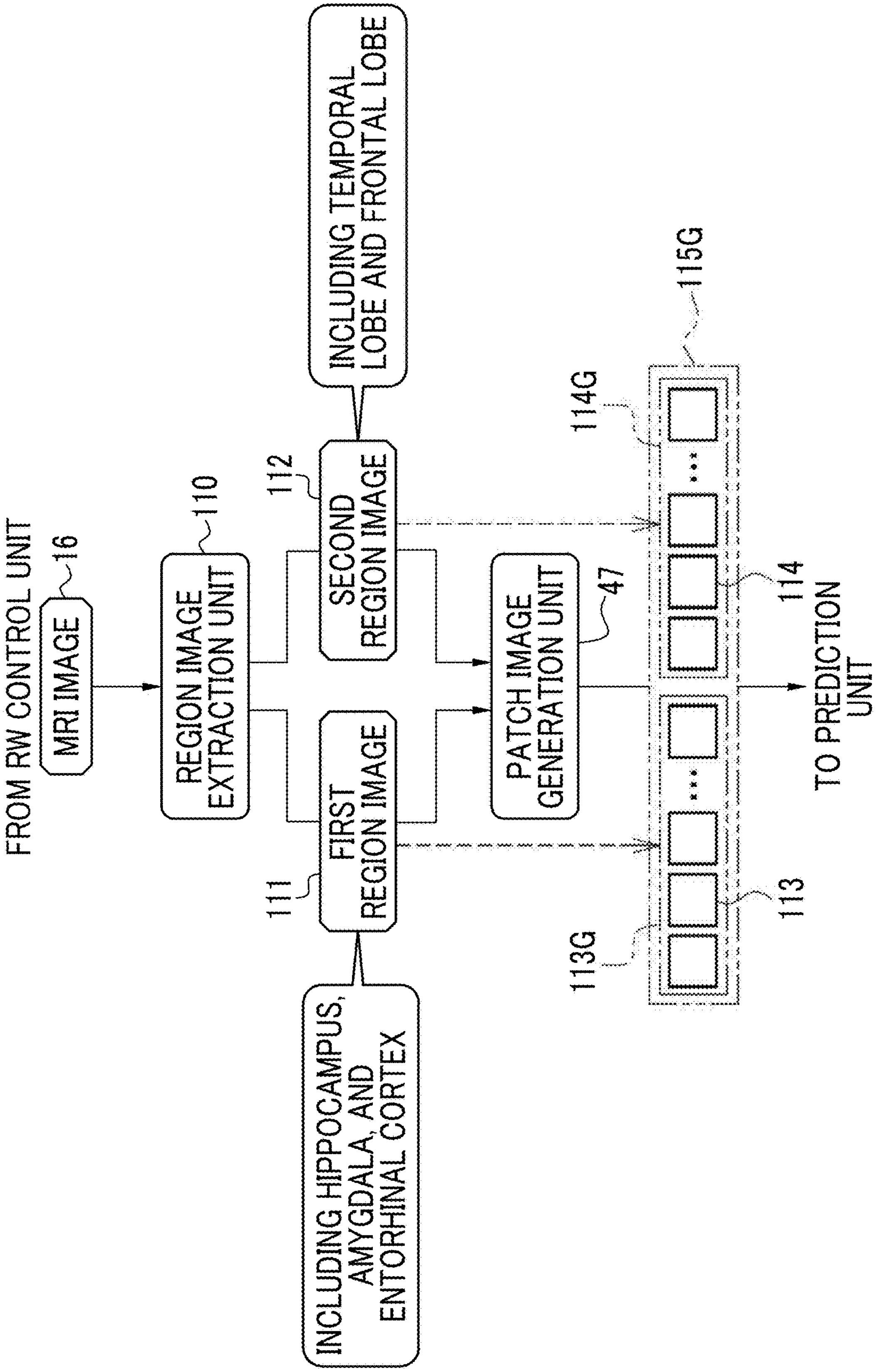
FIG. 12 is a block diagram showing a processing unit and an outline of processing of a CPU of an information processing server according to a second embodiment.

As shown in FIG. 12 as an example, the CPU of the information processing server according to the second embodiment functions as a region image extraction unit 110 in addition to the processing units 45 to 49 according to the first embodiment (only the patch image generation unit 47 is shown in FIG. 12). The region image extraction unit 110 is provided before the patch image generation unit 47. The MRI image 16 is input to the region image extraction unit 110 from the RW control unit 46. The region image extraction unit 110 extracts a first region image 111 and a second region image 112 from the MRI image 16, for example, by using a semantic segmentation model that performs class labeling on each anatomical region of the brain. The first region image 111 is an image of a region of the brain mainly centered on the hippocampus, and includes the hippocampus, the amygdala, and the entorhinal cortex. The second region image 112 is an image of a region of the brain mainly centered on the temporal lobe, and includes the temporal lobe and the frontal lobe. The region image extraction unit 110 outputs the first region image 111 and the second region image 112 to the patch image generation unit 47.

The patch image generation unit 47 subdivides the first region image 111 into a plurality of first patch images 113. In addition, the patch image generation unit 47 subdivides the second region image 112 into a plurality of second patch images 114. Therefore, a patch image group 115G in this case is composed of a first patch image group 113G which is a set of the plurality of first patch images 113 and a second patch image group 114G which is a set of the plurality of second patch images 114. The patch image generation unit 47 outputs the patch image group 115G to the prediction unit 48. Since the subsequent processing is the same as that of the first embodiment, the description thereof is omitted.

Here, the hippocampus is related to memory and spatial learning ability. The amygdala plays a major role in the formation and storage of memory associated with an emotional event. The entorhinal cortex is a region necessary for episodic memory to function normally.

The temporal lobe is an essential region for auditory perception, language reception, visual memory, language memory, and emotion. For example, in a case where a lesion occurs in the right temporal lobe, it is generally impossible to interpret a non-verbal auditory stimulus (for example, music). In addition, in a case where a lesion occurs in the left temporal lobe, recognition, memory, and organization of language are severely impaired. The frontal lobe is responsible for a function of initiating or inhibiting a person's action. In addition, the frontal lobe also plays a role of organizing, planning, processing, and determining information necessary for daily life. In addition, person can objectively perceive himself/herself, have emotions, and further speak words because the frontal lobe functions.

In the second embodiment, the region image extraction unit 110 extracts the first region image 111 including the hippocampus, the amygdala, and the entorhinal cortex and the second region image 112 including the temporal lobe and the frontal lobe, from the MRI image 16. Then, the patch image generation unit 47 subdivides the first region image 111 into the plurality of first patch images 113 and subdivides the second region image 112 into the plurality of second patch images 114. The first patch image 113 and the second patch image 114 include anatomical regions that are important for predicting the progression of the dementia, such as the hippocampus, the amygdala, the entorhinal cortex, the temporal lobe, and the frontal lobe. Therefore, it is possible to further increase the prediction accuracy of the prediction result 18 related to the dementia by the prediction model 41.

The medical image is not limited to the MRI image 16. Instead of the MRI image 16 or in addition to the MRI image 16, another morphological image test data such as a CT image, or brain function image test data such as a PET image or a SPECT image may be used.

The cognitive function test data may be a rivermead behavioural memory test (RBMT) score, a score of activities of daily living (ADL), or the like. In addition, the cognitive function test data may be a score of ADAS-Cog, a score of MMSE, or the like. A plurality of types of the cognitive function test data may be included in the dementia-related data 17.

The CSF test data is not limited to the amount of p-tau 181 shown as an example. The CSF test data may be the amount of total tau protein (t-tau) or the amount of amyloid β protein (Aβ42).

The prediction result 18 is not limited to the content indicating whether the subject will or will not suffer from Alzheimer's dementia within 2 years. For example, the prediction result 18 may have a content that a degree of progression of the Alzheimer's dementia in the subject after 3 years is fast/slow. The prediction result 18 may be a probability of each of normal, mild cognitive impairment, and Alzheimer's dementia. The prediction result 18 may be a change amount of the cognitive function test data.

The prediction result 18 is not limited to Alzheimer's dementia, and more generally, the prediction result 18 may have a content that the subject is any one of normal, preclinical AD, mild cognitive impairment, or dementia. Subjective cognitive impairment (SCI) and/or subjective cognitive decline (SCD) may be added as a prediction target. In addition, the prediction result 18 may have a content indicating whether or not the subject progresses to MCI from normal or preclinical AD or whether or not the subject progresses to Alzheimer's dementia from normal, preclinical AD, or MCI.

The prediction includes prediction of a cognitive function, such as how much the cognitive function of the subject is reduced after, for example, two years, prediction of a risk of developing the dementia, such as a degree of the risk of developing the dementia of the subject, and the like.

Instead of distributing the prediction result 18 itself from the information processing server 10 to the user terminal 11, screen data including the prediction result 18 may be distributed from the information processing server 10 to the user terminal 11. In addition, the aspect in which the prediction result 18 is provided for viewing by the doctor is not limited to the aspect in which the prediction result 18 is distributed to the user terminal 11. A printed matter of the prediction result 18 may be provided to the doctor, or an electronic mail with the prediction result 18 attached may be transmitted to a portable terminal of the doctor.

The learning of the prediction model 41 shown in FIG. 10 may be performed in the information processing server 10 or may be performed in an apparatus other than the information processing server 10. In addition, the learning of the prediction model 41 may be continued even after the operation. In a case of training the prediction model 41 in the information processing server 10, the information processing server 10 is an example of a "learning apparatus" according to the technology of the present disclosure. In a case of training the prediction model 41 in an apparatus other than the information processing server 10, the apparatus other than the information processing server 10 is an example of a "learning apparatus" according to the technology of the present disclosure.

The information processing server 10 may be installed in each medical facility or may be installed in a data center independent of the medical facility. In addition, the user terminal 11 may have a part or all of the functions of the processing units 45 to 49 of the information processing server 10.

Although dementia has been exemplified as the disease, the present disclosure is not limited to this. The disease may be, for example, cerebral infarction. In this case, the CT image or the MRI image showing the brain of the subject and the disease-related data such as the age and the sex of the subject are input to the prediction model, and a change amount of a National Institutes of Health Stroke Scale (NIHSS) score or a change amount of a Japan Stroke Scale (JSS) score is output from the prediction model as the prediction result. The disease is preferably a cranial nerve disease including a neurodegenerative disease and a cerebrovascular disease such as the exemplified dementia and cerebral infarction, or Parkinson's disease. As described above, the prediction includes the prediction for the progression of the disease and/or the prediction for the diagnosis support of the disease.

Note that the dementia has become a social problem with the advent of an aging society in recent years. Therefore, the present example in which the disease is dementia can be said to be a form that matches the current social problem.

The disease is not limited to the cranial nerve disease, and thus the organ is not limited to the brain.

In each of the above-described embodiments, for example, as a hardware structure of a processing unit that executes various types of processing, such as the reception unit 45, the RW control unit 46, the patch image generation unit 47, the prediction unit 48, the distribution control unit 49, and the region image extraction unit 110, various processors shown below can be used. As described above, the various processors include, in addition to the CPU 32 that is a general-purpose processor which executes software (operation program 40) to function as various processing units, a programmable logic device (PLD) that is a processor of which a circuit configuration can be changed after manufacture, such as a field programmable gate array (FPGA), and a dedicated electrical circuit that is a processor having a circuit configuration which is designed for exclusive use to execute specific processing, such as an application specific integrated circuit (ASIC).

One processing unit may be configured of one of the various processors or may be configured of a combination of two or more processors of the same type or different types (for example, a combination of a plurality of FPGAs and/or a combination of a CPU and an FPGA). In addition, a plurality of processing units may be configured of one processor.

As an example of configuring the plurality of processing units with one processor, first, there is a form in which, as typified by computers such as a client and a server, one processor is configured of a combination of one or more CPUs and software and the processor functions as the plurality of processing units. Second, there is a form in which, as typified by a system on chip (SoC) and the like, a processor that implements functions of an entire system including the plurality of processing units with one integrated circuit (IC) chip is used. As described above, the various processing units are configured using one or more of the various processors as a hardware structure.

In addition, more specifically, an electric circuit (circuitry) in which circuit elements, such as semiconductor elements, are combined can be used as the hardware structure of these various processors.

It is possible to understand the techniques described in following Appendices from the above description.

Appendix 1

An information processing apparatus comprising: a processor, in which the processor acquires a medical image showing an organ of a subject and disease-related data of the subject, subdivides the medical image into a plurality of patch images, uses a prediction model including a feature amount extraction unit that extracts a feature amount from the patch images and the disease-related data and a correlation information extraction unit that extracts at least correlation information between the plurality of patch images and correlation information between the plurality of patch images and the disease-related data, and inputs the patch images and the disease-related data to the prediction model and outputs a prediction result regarding a disease from the prediction model.

Appendix 2

The information processing apparatus according to Appendix 1, in which the prediction model includes a transformer encoder that takes in input data in which the patch images and the disease-related data are mixed and extracts the feature amount.

Appendix 3

The information processing apparatus according to Appendix 2, in which the feature amount extraction unit includes a self-attention mechanism layer of the transformer encoder, and the correlation information extraction unit includes a linear transformation layer that linearly transforms the input data to the self-attention mechanism layer to obtain first transformation data, an activation function application layer that applies an activation function to the first transformation data to obtain second transformation data, and a calculation unit that calculates a product of output data from the self-attention mechanism layer and the second transformation data for each element as the correlation information.

Appendix 4

The information processing apparatus according to any one of Appendices 1 to 3, in which the disease is dementia, the medical image is an image showing a brain of the subject, and the processor extracts a first region image including a hippocampus, an amygdala, and an entorhinal cortex and a second region image including a temporal lobe and a frontal lobe from the medical image, and subdivides the first region image and the second region image into the plurality of patch images.

Appendix 5

The information processing apparatus according to any one of Appendices 1 to 4, in which the disease is dementia, the medical image is morphological image test data, and the disease-related data includes at least one of an age, a sex, blood/cerebrospinal fluid test data, genetic test data, or cognitive function test data of the subject.

Appendix 6

The information processing apparatus according to Appendix 5, in which the morphological image test data is a tomographic image obtained by a nuclear magnetic resonance imaging method.

In the technology of the present disclosure, the above-described various embodiments and/or various modification examples may be combined with each other as appropriate. In addition, it is needless to say that the present disclosure is not limited to each of the above-described embodiments, and various configurations can be used without departing from the gist of the present disclosure. Further, the technology of the present disclosure extends to a storage medium that non-transitorily stores a program in addition to the program.

The above descriptions and illustrations are detailed descriptions of portions related to the technology of the present disclosure and are merely examples of the technology of the present disclosure. For example, description related to the above configurations, functions, actions, and effects is description related to an example of configurations, functions, actions, and effects of the parts according to the embodiment of the disclosed technology. Therefore, unnecessary portions may be deleted or new elements may be added or replaced in the above descriptions and illustrations without departing from the gist of the technology of the present disclosure. Further, in order to avoid complications and facilitate understanding of the parts related to the technology of the present disclosure, descriptions of common general knowledge and the like that do not require special descriptions for enabling the implementation of the technology of the present disclosure are omitted, in the contents described and shown above.

In the present specification, the term "A and/or B" is synonymous with the term "at least one of A or B". That is, the term "A and/or B" means only A, only B, or a combination of A and B. In addition, in the present specification, the same approach as "A and/or B" is applied to a case in which three or more matters are represented by connecting the matters with "and/or".

All documents, patent applications, and technical standards mentioned in the present specification are incorporated herein by reference to the same extent as in a case in which each document, each patent application, and each technical standard are specifically and individually described by being incorporated by reference.

What is claimed is:

1. An information processing apparatus comprising:
- a processor,
- wherein the processor
  - acquires a medical image showing an organ of a subject and disease-related data of the subject,
  - subdivides the medical image into a plurality of patch images,
  - uses a prediction model including a feature amount extraction unit that extracts a feature amount from the patch images and the disease-related data and a correlation information extraction unit that extracts at least correlation information between the plurality of patch images and correlation information between the plurality of patch images and the disease-related data, and
  - inputs the patch images and the disease-related data to the prediction model and outputs a prediction result regarding a disease from the prediction model,
- wherein the prediction model includes a transformer encoder that takes in input data in which the patch images and the disease-related data are mixed and extracts the feature amount,
- wherein the feature amount extraction unit includes a self-attention mechanism layer of the transformer encoder, and
- wherein the correlation information extraction unit includes:
  - a linear transformation layer that linearly transforms the input data to the self-attention mechanism layer to obtain first transformation data,
  - an activation function application layer that applies an activation function to the first transformation data to obtain second transformation data, and
  - a calculation unit that calculates a product of output data from the self-attention mechanism layer and the second transformation data for each element as the correlation information.

2. The information processing apparatus according to claim 1,
- wherein the disease is dementia,
- the medical image is an image showing a brain of the subject, and
- the processor
  - extracts a first region image including a hippocampus, an amygdala, and an entorhinal cortex and a second region image including a temporal lobe and a frontal lobe from the medical image, and
  - subdivides the first region image and the second region image into the plurality of patch images.

3. The information processing apparatus according to claim 1,
- wherein the disease is dementia,
- the medical image is morphological image test data, and
- the disease-related data includes at least one of an age, a sex, blood/cerebrospinal fluid test data, genetic test data, or cognitive function test data of the subject.

4. The information processing apparatus according to claim 3,
- wherein the morphological image test data is a tomographic image obtained by a nuclear magnetic resonance imaging method.

5. An operation method of an information processing apparatus, the operation method comprising:
- acquiring a medical image showing an organ of a subject and disease-related data of the subject;
- subdividing the medical image into a plurality of patch images;
- using a prediction model including a feature amount extraction unit that extracts a feature amount from the patch images and the disease-related data and a correlation information extraction unit that extracts at least correlation information between the plurality of patch images and correlation information between the plurality of patch images and the disease-related data; and
- inputting the patch images and the disease-related data to the prediction model and outputting a prediction result regarding a disease from the prediction model,
- wherein the prediction model includes a transformer encoder that takes in input data in which the patch images and the disease-related data are mixed and extracts the feature amount, wherein the feature amount extraction unit includes a self-attention mechanism layer of the transformer encoder, and wherein the correlation information extraction unit includes:

a linear transformation layer that linearly transforms the input data to the self-attention mechanism layer to obtain first transformation data, an activation function application layer that applies an activation function to the first transformation data to obtain second transformation data, and a calculation unit that calculates a product of output data from the self-attention mechanism layer and the second transformation data for each element as the correlation information.

6. A non-transitory computer-readable storage medium storing an operation program of an information processing apparatus, the program causing a computer to execute:

acquiring a medical image showing an organ of a subject and disease-related data of the subject;

subdividing the medical image into a plurality of patch images;

using a prediction model including a feature amount extraction unit that extracts a feature amount from the patch images and the disease-related data and a correlation information extraction unit that extracts at least correlation information between the plurality of patch images and correlation information between the plurality of patch images and the disease-related data; and inputting the patch images and the disease-related data to the prediction model and outputting a prediction result regarding a disease from the prediction model, wherein the prediction model includes a transformer encoder that takes in input data in which the patch images and the disease-related data are mixed and extracts the feature amount, wherein the feature amount extraction unit includes a self-attention mechanism layer of the transformer encoder, and wherein the correlation information extraction unit includes:

a linear transformation layer that linearly transforms the input data to the self-attention mechanism layer to obtain first transformation data, an activation function application layer that applies an activation function to the first transformation data to obtain second transformation data, and a calculation unit that calculates a product of output data from the self-attention mechanism layer and the second transformation data for each element as the correlation information.

7. A non-transitory computer-readable storage medium storing a prediction model for causing a computer to function to output a prediction result regarding a disease in response to an input of a plurality of patch images obtained by subdividing a medical image showing an organ of a subject and disease-related data of the subject, the prediction model comprising:

a feature amount extraction unit that extracts a feature amount from the patch images and the disease-related data; and a correlation information extraction unit that extracts at least correlation information between the plurality of patch images and correlation information between the plurality of patch images and the disease-related data, wherein the prediction model includes a transformer encoder that takes in input data in which the patch images and the disease-related data are mixed and extracts the feature amount, wherein the feature amount extraction unit includes a self-attention mechanism layer of the transformer encoder, and wherein the correlation information extraction unit includes:

a linear transformation layer that linearly transforms the input data to the self-attention mechanism layer to obtain first transformation data, an activation function application layer that applies an activation function to the first transformation data to obtain second transformation data, and a calculation unit that calculates a product of output data from the self-attention mechanism layer and the second transformation data for each element as the correlation information.

8. A learning apparatus that provides a prediction model with a learning medical image and a learning disease-related data as learning data, and trains the prediction model to obtain a prediction result regarding a disease as an output in response to an input of a plurality of patch images obtained by subdividing a medical image showing an organ of a subject and disease-related data of the subject, wherein the prediction model includes:

a feature amount extraction unit that extracts a feature amount from the patch images and the disease-related data, a correlation information extraction unit that extracts at least correlation information between the plurality of patch images and correlation information between the plurality of patch images and the disease-related data, and a transformer encoder that takes in input data in which the patch images and the disease-related data are mixed and extracts the feature amount, wherein the feature amount extraction unit includes a self-attention mechanism layer of the transformer encoder, and wherein the correlation information extraction unit includes:

a linear transformation layer that linearly transforms the input data to the self-attention mechanism layer to obtain first transformation data, an activation function application layer that applies an activation function to the first transformation data to obtain second transformation data, and a calculation unit that calculates a product of output data from the self-attention mechanism layer and the second transformation data for each element as the correlation information.

9. A learning method of providing a prediction model with a learning medical image and a learning disease-related data as learning data, and training the prediction model to obtain a prediction result regarding a disease as an output in response to an input of a plurality of patch images obtained by subdividing a medical image showing an organ of a subject and disease-related data of the subject, wherein the prediction model includes;

a feature amount extraction unit that extracts a feature amount from the patch images and the disease-related data, a correlation information extraction unit that extracts at least correlation information between the plurality of patch images and correlation information between the plurality of patch images and the disease-related data, and a transformer encoder that takes in input data in which the patch images and the disease-related data are mixed and extracts the feature amount, wherein the feature amount extraction unit includes a self-attention mechanism layer of the transformer encoder, and wherein the correlation information extraction unit includes:

a linear transformation layer that linearly transforms the input data to the self-attention mechanism layer to obtain first transformation data, an activation function application layer that applies an activation function to the first transformation data to obtain second transformation data, and a calculation unit that calculates a product of output data from the self-attention mechanism layer and the second transformation data for each element as the correlation information.

* * * * *